(12) United States Patent
Gulka et al.

(10) Patent No.: US 8,181,591 B1
(45) Date of Patent: May 22, 2012

(54) DOMED ACTUATOR FOR INDICATING DEVICE

(75) Inventors: Noel Gulka, London (CA); Greg Lawrence, London (CA); Michael Nuttall, London (CA)

(73) Assignee: Trudell Medical International, London (CA)

( * ) Notice: Subject to any disclaimer, the term of this patent is extended or adjusted under 35 U.S.C. 154(b) by 248 days.

(21) Appl. No.: 12/470,259

(22) Filed: May 21, 2009

Related U.S. Application Data

(60) Provisional application No. 61/055,612, filed on May 23, 2008.

(51) Int. Cl.
*A61M 15/00* (2006.01)
*B67D 7/22* (2010.01)

(52) U.S. Cl. .................. 116/285; 116/307; 128/205.23; 128/200.14; 222/36

(58) Field of Classification Search .............. 116/285, 116/299, 306, 307, 309, 312, 314, DIG. 1; 128/200.14, 205.23; 206/528, 459.1, 459.5; 235/1 B, 1 C, 113, 140; 222/23, 36; 221/2, 221/8
See application file for complete search history.

(56) References Cited

U.S. PATENT DOCUMENTS

| | | |
|---|---|---|
| 165,054 A | 6/1875 | Baldwin |
| 498,851 A | 6/1893 | Jones |
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Sheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |

(Continued)

FOREIGN PATENT DOCUMENTS

AU 598250 B2 6/1990

(Continued)

OTHER PUBLICATIONS

International Search Report in International Application No. PCT/IB2005/002764, dated Feb. 21, 2006, 8 pages.

(Continued)

*Primary Examiner* — Amy Cohen Johnson
(74) *Attorney, Agent, or Firm* — Brinks Hofer Gilson & Lione

(57) ABSTRACT

An indicating device includes a first housing component adapted to be mounted to a container and a second housing component moveably connected to the first housing component. The second housing component is moveable relative to the first housing component along an axial path. The second housing component includes an exposed actuation surface having a substantially convex domed shape. The exposed actuation surface of the second housing component can include a lubricant. A method of actuating an indicating device is also provided.

21 Claims, 3 Drawing Sheets

U.S. PATENT DOCUMENTS

| | | |
|---|---|---|
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Amrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |

| | | |
|---|---|---|
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | De La Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,988,496 A | 11/1999 | Bruna |
| 5,988,946 A | 11/1999 | Reed |
| 6,000,159 A | 12/1999 | Hornung |
| 6,012,450 A | 1/2000 | Rubsamen |
| 6,029,659 A | 2/2000 | O'Connor |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,183,087 B1 | 2/2001 | Kirkpatrick et al. |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | De La Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,901,629 B2 * | 6/2005 | Wurdack .................... 16/42 R |
| 6,907,876 B1 | 6/2005 | Clark et al. |
| 7,004,164 B2 | 2/2006 | Scarrott |
| 7,137,391 B2 | 11/2006 | Bruna |
| 7,143,764 B1 | 12/2006 | Dagsland et al. |
| 7,156,258 B2 | 1/2007 | Eckert |
| 2002/0000225 A1 | 1/2002 | Schuler et al. |
| 2002/0153005 A1 | 10/2002 | Scarrott et al. |
| 2003/0183225 A1 | 10/2003 | Knudsen |
| 2003/0200964 A1 | 10/2003 | Blakley et al. |
| 2003/0205227 A1 | 11/2003 | Hodson |
| 2003/0209239 A1 | 11/2003 | Rand et al. |
| 2004/0065326 A1 | 4/2004 | MacMichael et al. |
| 2004/0069301 A1 | 4/2004 | Bacon |
| 2004/0094147 A1 | 5/2004 | Schyra et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0211420 A1 | 10/2004 | Minshull et al. |
| 2004/0221840 A1 | 11/2004 | Stockman-Lamb |
| 2004/0255935 A1 | 12/2004 | Bruna |
| 2004/0255936 A1 | 12/2004 | Urbanus |
| 2005/0011515 A1 | 1/2005 | Lee et al. |
| 2005/0056276 A1 | 3/2005 | Schuler et al. |
| 2005/0268905 A1 | 12/2005 | Rasmussen et al. |
| 2005/0284471 A1 | 12/2005 | Bruna |
| 2006/0254581 A1 | 11/2006 | Genova et al. |
| 2007/0084462 A1 | 4/2007 | Allen |

FOREIGN PATENT DOCUMENTS

| | | |
|---|---|---|
| CA | 535518 | 1/1957 |
| CA | 2 152 088 A | 7/1994 |
| CA | 2 181 789 C | 6/1996 |
| CA | 2 190 204 C | 5/1997 |
| CA | 2 293 484 A | 12/1998 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| CA | 2 480 035 A1 | 10/2003 |
| DE | 6 603 758 | 7/1969 |
| DE | 27 02 539 A1 | 1/1977 |
| DE | 33 36 486 A1 | 4/1984 |
| DE | 85 90 143.1 | 10/1985 |
| DE | 86 02 238 | 5/1986 |
| EP | 0 028 929 A2 | 5/1981 |
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 752 895 B1 | 7/1998 |
| EP | 0 949 584 A2 | 10/1999 |

| | | |
|---|---|---|
| EP | 1 369 139 A1 | 12/2003 |
| EP | 1 220 802 B1 | 2/2004 |
| FR | 2 743 055 | 7/1997 |
| GB | 998 148 | 7/1965 |
| GB | 1 058 636 | 2/1967 |
| GB | 1 290 484 | 9/1972 |
| GB | 1 317 315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 372 543 A | 8/2002 |
| GB | 2 414 187 A | 11/2005 |
| GB | 2 434 754 A | 8/2007 |
| JP | 61-55759 | 4/1986 |
| JP | 04-50059 | 4/1992 |
| JP | 6-26891 | 4/1994 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/26769 | 10/1995 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/59806 | 10/2000 |
| WO | WO 01/28887 A1 | 4/2001 |
| WO | WO 01/29765 A1 | 4/2001 |
| WO | WO 01/37909 A1 | 5/2001 |
| WO | WO 03/101514 A1 | 12/2003 |
| WO | WO 03/103759 A1 | 12/2003 |
| WO | WO 2004/026380 A2 | 4/2004 |
| WO | WO 2004/089451 A1 | 10/2004 |
| WO | WO 2006/110080 A1 | 10/2006 |
| WO | WO 2007/034237 A1 | 3/2007 |
| WO | WO 2007/103712 A2 | 9/2007 |

OTHER PUBLICATIONS

Written Opinion in International Application No. PCT/IB2005/002764, dated Feb. 21, 2006, 5 pages.

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

"Geneva drive," Wikipedia [online] [retrieved from internet: URL: http://en.wikipedia.org/wiki/Geneva_drive] [retrieved on Sep. 24, 2007], 3 pages.

English language translation of Office Action in Japanese Application No. 2008-019458 dispatched Sep. 29, 2009, 2 pages.

Bespak Presentation, 2007, 6 pages.

* cited by examiner

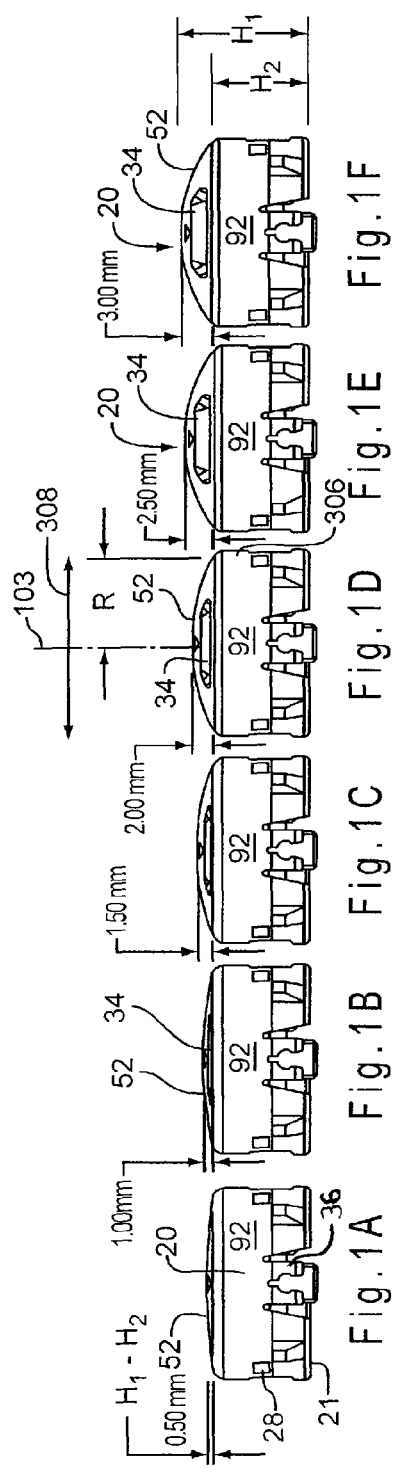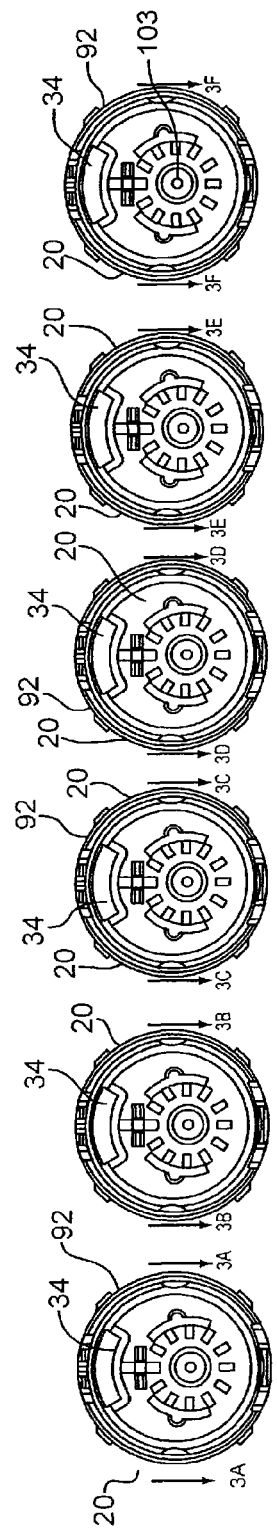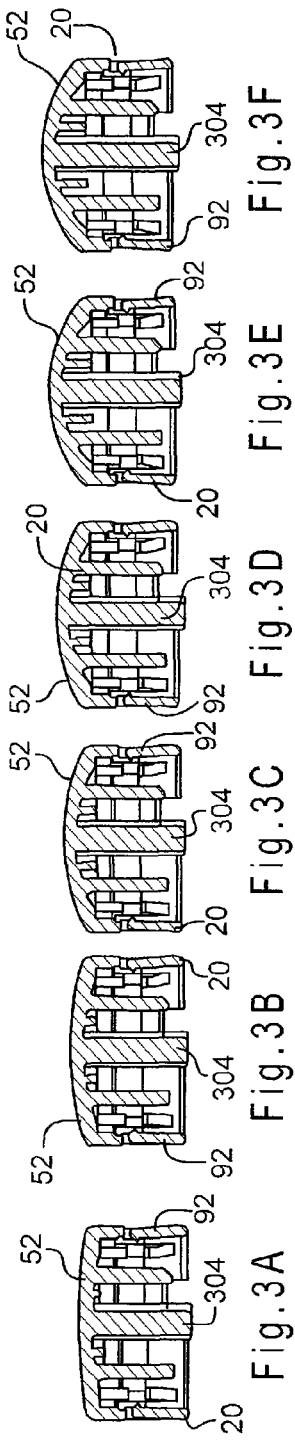

DOMED ACTUATOR FOR INDICATING DEVICE

This application claims the benefit of U.S. Provisional Patent Application No. 61/055,612, filed May 23, 2008, the entire disclosure of which is hereby incorporated herein by reference.

FIELD OF THE INVENTION

The present invention relates generally to an indicating device, and in particular, to an indicating device having a domed actuator.

BACKGROUND

Various dispensing devices have been developed where it is desirable to provide information about the number of discharges of a particular substance that have been dispensed from or remain in a container. For example, various aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

In order to provide an accurate indication, some devices are provided with a dose indicator secured to an end of the container, with an actuation force being applied to the dose indicator so as to actuate the dose indicator and the container. In such a system, the force required to actuate the dose indicator must be tuned such that it is not greater than the force required to actuate the container, which could result in an uncounted actuation. Conversely, the force required to actuate the dose indicator cannot be so minimal as to count an actuation when such an event has not transpired.

Some dose indicator devices include a first member (e.g., a cap member) moving along an axis relative to a second member (e.g., a base member secured to the container) in response to a force applied to the first member. In some embodiments, one of the cap or base members has a center post received in a corresponding socket of the other member. If the force applied to the first member is radially spaced (off-center) from the axis, the first member may tilt relative to the second member, which can then cause an increase in friction, for example along the center post or between nested, circumferential walls of the first and second members. This friction force, in turn, increases the force required to actuate the dose counter, which may then not be tuned with the actuation force of the corresponding container.

SUMMARY

Briefly stated, one preferred embodiment of an indicating device includes a first housing component adapted to be mounted to a container and a second housing component moveably connected to the first housing component. The second housing component is moveable relative to the first housing component along an axial path. The second housing component has an exposed actuation surface extending between a center axis and an outer peripheral edge of the second housing component. The actuation surface has a substantially convex domed shape such that a tangent along any point of at least the outer one half peripheral portion of the actuation surface forms an angle relative to a plane formed substantially perpendicular to the axial path, wherein the angle is greater than 0 degrees and less than or equal to 90 degrees. An indicator member is disposed in at least one of said first and second housing components.

In another aspect, one embodiment of an indicating device includes a first housing component adapted to be mounted to a container and a second housing component moveably connected to the first housing component. The second housing component is moveable relative to the first housing component along an axial path. The second housing component has an exposed actuation surface having a substantially convex domed shape. An indicator member is disposed in at least one of the first and second housing components. The exposed actuation surface of the second housing component includes a lubricant.

In yet another aspect, one embodiment of a method for indicating the amount of substance that have been dispensed from or remain in a container includes providing a first housing component adapted to be mounted to a container, a second housing component moveably connected to the first housing component and a biasing member disposed between the first and second housing components. The second housing component includes an exposed actuation surface extending between a center axis and an outer peripheral edge of said second housing component, wherein the actuation surface has a substantially convex domed shape. The method further includes applying an axial force to an outer peripheral portion of the actuation surface of the second housing component relative to the first housing component along an axial path, wherein the axial force is greater than a biasing force applied by the biasing member. The method further includes applying a lateral force to the outer peripheral portion sufficient to maintain contact with the actuation surface and rotating an indicator member disposed in at least one of the first and second housing components in response to one or more applications the axial force.

The presently preferred embodiments provide significant advantages over other dispensing devices and indicating devices used therewith. In particular, the shape and configuration of the second housing component are such that the user is either forced to actuate the device close to the center axis of the second housing component, or apply a lateral force to the second housing component in combination with the longitudinal force so as to maintain engagement between the user's finger(s) and the second housing component. In the first instance, the moment between the force and the axis are minimal, thereby producing minimal frictional forces between the first and second housing members. In the second instance, the lateral force applied by the user results in a moment that counters the moment produced by the offset longitudinal force, thereby again reducing or minimizing the frictional forces and thereby maintaining a relative uniform actuation force.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIGS. 1A-F are side views of various configurations of an actuator housing component.

FIGS. 2A-F are bottom views of the housing components shown in FIGS. 1A-F.

FIGS. 3A-F are sectional views of the housing components shown in FIGS. 2A-F taken along respective lines 3A-F.

FIG. 9 is a cross-sectional view of the indicating device similar to

FIG. 6 showing the first housing component as it returns to the fully extended position relative to the second housing component as indicated by the directional arrows.

DETAILED DESCRIPTION OF THE PRESENTLY PREFERRED EMBODIMENTS

Figure 11:
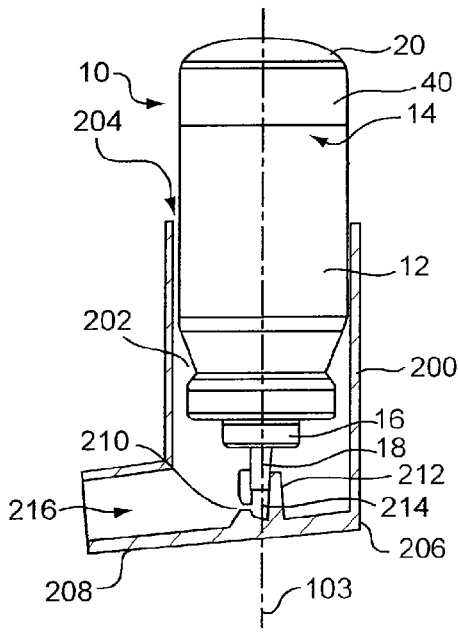
FIG. 11 is a cross-sectional side view of an indicating device applied to the bottom of a container supported in a dispenser housing.

Referring to the drawings, and in particular FIG. 11, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through opening 204 and be installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIG. 11.

As shown in FIG. 11, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

The container 12 is cylindrical and has a hub 16 disposed on a top surface 17 thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a pressurized aerosol and medicament which is dispensed therefrom in specific metered doses by an actuation thereof effected by depressing or moving the valve stem 18 from an extended closed position to a depressed open position. A single metered dose is dispensed from the container by each reciprocal, longitudinal movement of the valve stem, or actuation of the container.

In operation, the opening of the valve stem is effected by moving the container 12 reciprocally within the housing 200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of aerosol and medicament through the well 214 and orifice 210. The aerosol and medicament are then transmitted to the patient through the exhaust port 216 of the mouthpiece by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of medicament upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament. It should be understood that other dispensing devices, other than aerosol devices, are configured to sequentially dispense substances, including without limitation other medical dispensing devices such as powder inhalers and other dispensers.

Now generally referring to the FIGS. 1-11, a dispenser indicating device is shown. The indicating device 10 indicates, for example, the number of metered doses that have been dispensed from or remain in the container. As shown in the embodiment of FIG. 11, respectively, the indicating device 10 includes an indicating device housing having a first housing component, shown as a cap member 20, disposed in a second housing component, shown as a base member 40. It should be understood that the terms "first" and "second" can be used interchangeably, with the base member referred to as a first housing component and the cap member as a second housing component. The base member 40 is configured such that it can be mounted to the bottom end 14 of the container 12. In one embodiment, the base member 40 includes a convex, or curved bottom portion, or floor, which is shaped to be received in and to mate with the bottom end 14 of the container, which has a concave or inwardly curved contour. The base member 40 is preferably bonded to the bottom of the container with adhesive, double sided tape, or similar bonding agent. In one embodiment, an adhesive wrap, such as a label, is wrapped around the indicating device and container, which in one embodiment have substantially the same outer diameter. In other embodiments (not shown), the base member can be configured with a downwardly depending circumferential skirt, which is shaped to receive the bottom end of the container. In such an embodiment, the base member is mounted on the container either by bonding one or more of the bottom portion or skirt to the container, and/or by press fitting the container in the base member so as to provide an interference fit between the container and the depending skirt.

Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section. In addition, it should be understood that the base member can be moveably received in the cap member. Various indicating devices are shown in U.S. Pat. No. 7,004,164, issued Feb. 26, 2006, and U.S. Pat. No. 6,729,330, issued May 4, 2004, the entire disclosures of which are hereby incorporated herein by reference.

As best shown in FIGS. 1F and 2F, the cap member 20 has a top portion 52 with a viewing window 34 formed therein. Preferably, the cap member 20 is circular in cross-section and the viewing window is formed in the top portion adjacent the outer periphery of the cap member so as to overlie indicia applied to at least one indicator member 260 supported beneath the cap member. The viewing window 34 can be configured in a number of various shapes. For example, the viewing window can be tapered, arcuate shaped (bounded by coaxial inner and outer curved borders and radial side borders), or any other suitable shape. The top of the cap member preferably has a plurality of raised portions forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device. In addition, the viewing window can be formed in one or both of the cap member and base member, for example and without limitation in a side wall/skirts thereof.

Figure 5:
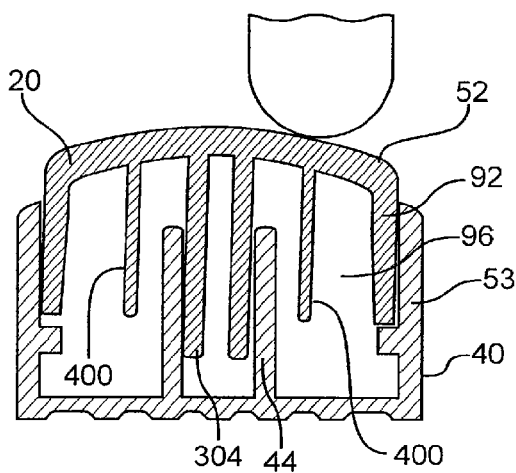
FIG. 5 is a cross-sectional view of an indicating device configured with a domed surface having an offset longitudinal force being applied thereto.
Figure 6:
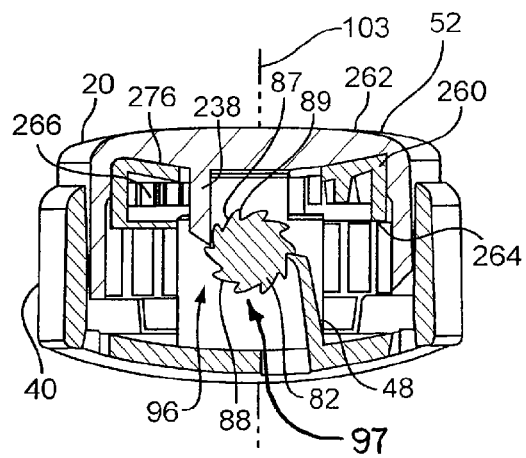
FIG. 6 is a cross-sectional view of the indicating device taken along wherein a first housing component is in a fully extended position relative to a second housing component prior to the application of an axial force by the user.
Figure 7:
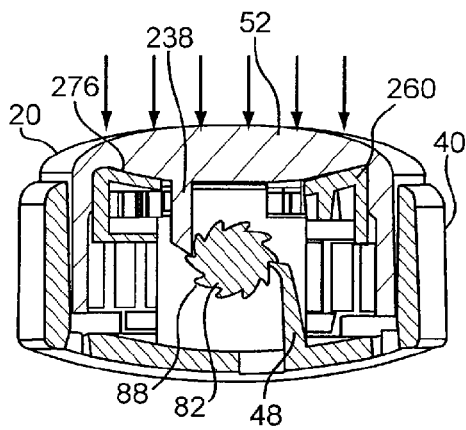
FIG. 7 is a cross-sectional view of the indicating device similar to FIG. 6 but with the first housing component shown as moving toward the second housing component at an intermediate position of the stroke as indicated by the directional arrows.
Figure 8:
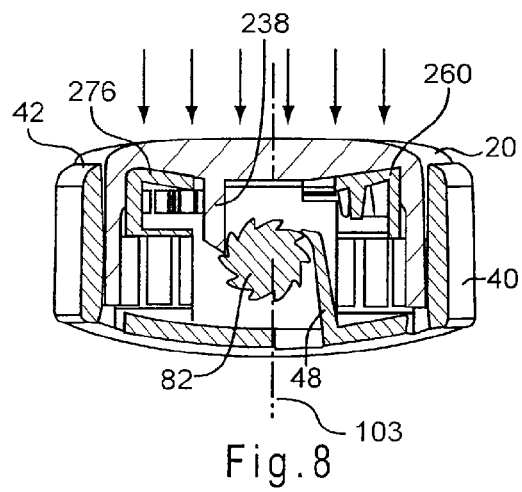
FIG. 8 is a cross-sectional view of the indicating device similar to FIG. 6 but with the first housing component reaching the bottom of the stroke as indicated by the directional arrows.
Figure 9:
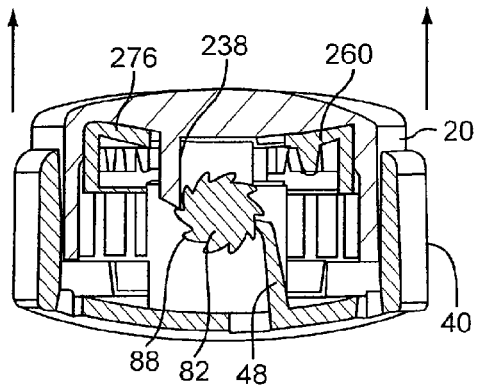

Referring to FIG. 5 the cap member 20 includes a circumferential skirt 92 depending downwardly from the top portion 52. The skirt preferably has a smaller diameter than an upwardly depending skirt 53 of the base member, such that the cap member skirt nests within the upwardly extending skirt of the base member. Alternatively, the cap member can be configured with a skirt having a larger diameter than the skirt of the base member such that the base member skirt nests in the cap member skirt. The cap member 20 is moveably mounted to the base member 40 by way of a snap fit.

For example, the cap member can include a plurality of engagement members 28 extending from an outer circumferential surface of the skirt. The cap member 20 is inserted axially within a recess or cavity 96 of the base member such that the engagement members 28, which have a tapered surface, slide past a rim 42 of the base member skirt until the engagement members are disposed in a plurality of pockets formed along the inner circumferential surface of the base member skirt to form a snap-lock fit. In particular, the upper surface of the engagement member 28 engages an engagement surface defining the top of the pocket. In this way, the cap member 20 is moveable with respect to the base member 40 along an axial, or longitudinal, path. Alternatively, the rim of the base member can be curved slightly inward such that the engagement members engage the inwardly curved rim portion so as to prevent the cap member from being separated from the base member.

The axial movement of the cap member 20 relative to the base member 40 is bounded or constrained by the engagement of the engagement members with the top of the base member pockets (or the base member rim) at a fully extended position and by engagement of a bottom rim 21 of the cap member skirt with a surface of the bottom portion of the base member at the bottom of the stroke. One of skill in the art should understand that the engagement members can alternatively be formed on the base member skirt so as to engage pockets or openings, or a rim (or like protrusion), formed on the cap member skirt.

Figure 10:
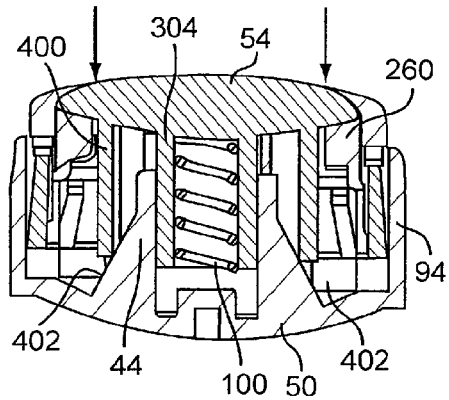
FIG. 10 is a cross-sectional view of the indicating device taken through the middle of the indicating device.
Figure 12:
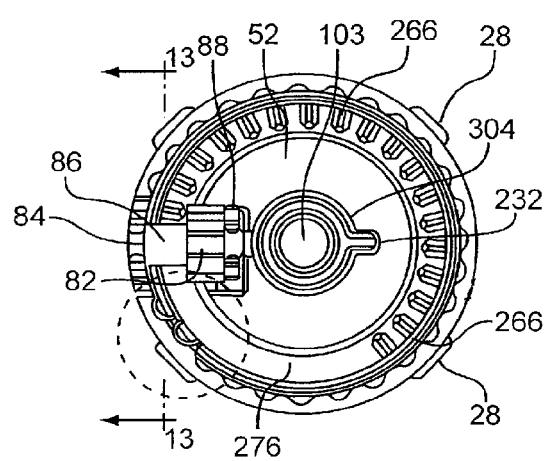
FIG. 12 is a bottom view of the indicating device.

As shown in FIG. 10, a spring 100 is disposed between the cap member and the base member. The spring is preferably disposed around or within an upwardly extending hub portion 44 of the base member, which mates with a post 304 extending downwardly from the top portion 52 of the cap member, with the hub and post portions 44, 304 functioning as guide members. As shown in FIG. 12, the hub and post portions can be configured with corresponding key portions 232, which prevents relative rotation between the cap member and base member, thereby ensuring proper engagement of the drive mechanism. The spring 100 functions as a return mechanism and biases the cap member 60 upwardly in the base member such that the engagement members 28 of the cap member engage the upper portion of the pockets of the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

Referring to FIGS. 6-10, 12 and 13, a first indicator member 260 is rotatably mounted in the cap member 20 about an axis 103 substantially parallel to the axial movement of the cap member relative to the base member, and preferably coaxially therewith. It should be understood that more than one indicator member, as disclosed for example in U.S. Pat. No. 6,729,330, the entire disclosure of which is hereby incorporated herein by reference, may also be used. The indicator member is also referred to herein as a driven member. The indicator member is generally open in the middle and includes an annular ring portion 276 having an upper surface that rotatably slides along a bottom surface of the top portion of the cap member. Alternatively, the indicator member can be mounted on the outside of the cap member with a viewing window formed in the indicator member for viewing indicia applied to the top of the cap member.

The annular ring portion 276 of the indicator member is rotatably secured to the cap member with a plurality of protrusions (not shown), or tab members, which extend from an inner circumferential surface of the cap member skirt. Alternatively, the indicator member can include an engagement member, or rim, that engages a groove or similar opening in the cap member. In this way, the indicator member is secured to the cap member so as to prevent axial movement therebetween but wherein the indicator member 260 is permitted to rotate relative to the cap member 20. The indicator member is installed by snap-fitting the indicator member within the cap member. One of skill in the art should understand that the indicator member could alternatively be rotatably mounted on the cap member hub portion, or on a similar axle secured to the cap member.

The indicator member 260 has a plurality of downwardly facing teeth 266 formed around the outer periphery on a bottom side of the annular ring member. The teeth are formed by recesses formed in the bottom of the annular ring member 276, with each recess having a leading engagement face and a curved trailing surface. The teeth 266 are formed in a circumferential ring around the periphery of the ring member 276.

Figure 13:
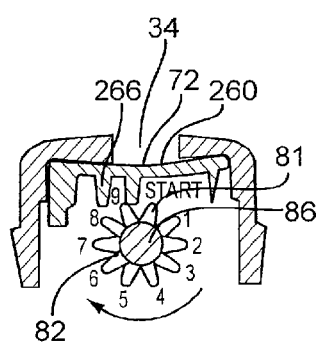
FIG. 13 is a cross-sectional view of the indicating device taken along line 13-13.

As shown in FIG. 13, dosage indicia 72 in the form of numbers or color codings are provided on the top surface of the indicator member and are visible to the user through the viewing window 34 provided in the top of the cap member. In one embodiment, the indicia are configured as numbers arranged sequentially from 0 to 200 around the upper surface of the annular ring 276. It should be understood that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid displayed in the viewing window could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container should be replaced, or, conversely, to go from the starting predetermined number to 0 (or some ending number), which again indicates to the user that the container should be replaced.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel. In various preferred alternative embodiments, one or both of the base member and cap member can be made of polycarbonate.

Referring to FIGS. 6-10, 12 and 13, a drive mechanism is shown as including a drive assembly 97. The drive assembly includes a ratchet wheel 82 coaxially mounted to a drive member 86 on an axle 84. The ratchet wheel, drive member and axle can be made separately, with the ratchet wheel and drive member then mounted on the axle, or all three parts can be integrally molded as a one-piece component. The drive assembly is preferably made of hard plastic material such as Acetel. In one embodiment, the drive assembly further includes a second dosage indicator member (not shown) coaxially mounted with and between the drive member 86 and ratchet wheel 82. The indicator member is configured as a wheel and preferably includes dosage indicia positioned around the peripheral surface thereof. Preferably, the indicia are comprised of consecutive numerals running from 0 to 9, and provide dispensing indicia to the user in combination with indicator member 260.

The ratchet wheel 82 includes a plurality of teeth 88 (preferably ten) formed around its periphery. Each of the teeth includes an engagement surface 89 and a tapered surface 87. The drive member 86, whether integrally formed with the ratchet wheel or separately connected thereto, includes a single tooth 89 extending radially from the axle 84.

The drive assembly is mounted to the cap member by engaging opposite ends of the axle 84 with downwardly extending hub portions 36 such that the axle, ratchet wheel and drive member rotate about an axis substantially perpendicular to the axial movement of the cap member relative to the base member and to the axis of rotation of the indicator member. Alternatively, the drive assembly can be mounted to the base member, along with the indicator member, in a similar manner.

The drive mechanism further includes a pawl member 48, shown as a flexible rod or finger, which extends upwardly from the bottom portion of the base member and selectively engages one of the teeth of the ratchet wheel. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member, also shown as a flexible rod or finger, extends downwardly from the top portion of the cap member and selectively engages another of the teeth 88 of the ratchet wheel. It should be understood that the pawl member could alternatively extend from the cap member (and the non-return member from the base member) when the drive assembly is mounted to the base member, as described above. Of course, when formed integrally with one or the other of the cap member and base member, the pawl member and non-return member are preferably made of the same materials as the respective cap member and base member.

In operation, the user depresses the cap 20 member from a fully extended position toward the base member such that the cap member bottoms out in the base member at the bottom of the stroke and such that the base member imparts an axial load on the container until a metered dosage is dispensed therefrom. In a preferred embodiment, the biasing force of the spring 100, or alternative return mechanism such as resilient arm members 400 which act as springs as the arm members 400 slide along ramped biasing surfaces 402 (see FIG. 10), is less than the biasing force of the spring located in the metering valve of the container, such that the cap member first bottoms out in the base member with the container then being moved downwardly in the housing until a metered dose is dispensed.

As the cap member 20 is depressed toward the base member 40, the pawl 48 selectively engages the engagement surface 89 of one of the ratchet wheel teeth and rotates the ratchet wheel. The tapered surface 87 of one of the teeth formed on the ratchet wheel simultaneously biases the non-return member 238 outwardly until it selectively engages the next tooth near the bottom of the stroke. The non-return member 38 provides an audible click as it engages the next tooth. The user then releases the cap member whereinafter the spring 100, or similar return mechanism, biases the cap member 20 away from the base member 40 until the engagement member engages the base portion at the top of the stroke. When the cap member is released by the user, the container is biased upwardly within the housing along the longitudinal axis such that the valve stem is moved to the closed position within the container. Simultaneously, as the cap member is released and allowed to move away from the base member, the pawl 48 is biased outwardly by the tapered surface 87 of one of the teeth on the ratchet wheel as the non-return member 38 prevents a backwards rotation thereof so as to maintain a unidirectional rotation of the ratchet wheel. At the top of the stroke, the pawl 48 is again placed in position for selective engagement with one of the teeth of the ratchet wheel. Again, the pawl provides an audible click as it engages the next tooth. In summary, on the down stroke the non-return member makes a clicking sound as it slides over one or more ratchet teeth, while on the up stroke, the pawl member also makes a clicking sound as it slides over one or more ratchet teeth. In this way, the ratchet wheel 82, and connected drive member 86, are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel will make one full revolution for every ten actuations of the indicator device and container, or a tenth of a revolution for each actuation. It should be understood that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl is biased outwardly by the tapered surface of one of the ratchet wheel teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

As shown in FIGS. 6-10, 12 and 13, the drive member 86 is shown as preferably having a single tooth 81 or segment. Therefore, upon every tenth actuation, the drive member 86 is rotated such that the tooth selectively engages one of the teeth 266 formed on the indicator member so as to rotate the indicator member 260 an incremental amount. The incremental amount of rotation is defined by the distance between adjacent teeth 266, otherwise defined as the circular pitch of the teeth. In this way, the drive member is selectively engaged with at least one of the teeth of the indicator member after and upon a predetermined number of axial movements of the cap member relative to the base member so as to rotate the indicator member the incremental amount. The predetermined of number axial movements required to cause the indicator member to rotate is defined by and dependent upon the reduction ratio of the ratchet wheel and drive member, which, in turn, is defined by dividing the number of teeth formed on the ratchet wheel by the number of teeth formed on the drive member. For example, as shown in the preferred embodiment, a ratchet wheel having ten teeth and a drive member having one tooth will result in an incremental movement of the indicator member, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

The ratchet wheel includes ten teeth. As the container is actuated ten times, the drive tooth 89 rotates around until it engages one of the teeth 66 on the indicator member 260. At this point, the indicator has completed a single cycle equal to the number of predetermined number of axial movements, which results or culminates in the incremental movement of the indicator member 260. The cycle is then repeated (by again making the predetermined number of axial movements) so as to again culminate in the incremental movement of the indicator member. Preferably, numerical indicia (tens counter) are applied so as to correlate to the preferred embodiment requiring ten axial movements for one incremental advancement of the indicator wheel, with numerical indicia 0-9 applied to the outer peripheral surface of the second indicator member, if used.

The ratchet wheel 82 and drive member 86 with their reduction ratio provide a simple but reliable mechanism for advancing the indicator member. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member 260. As such, the indicator member can be made with coarser teeth at less cost. In addition, larger coarser teeth interacting with a relatively large drive member tooth 89 helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses). This single revolution corresponds to a usage cycle, which is defined as the movement of the dosage indicator from an initial reading, which indicates that the container is full, to a final reading, which indicates that the container should be replaced. Of course, the indicator member, if initially set to a smaller number of dosages, may make less than a complete revolution in completing a usage cycle.

It should be understood that the indicator member or members could also be rotatably mounted to the base member, along with the drive mechanism, with the pawl extending from the cap member. In essence, either the cap member ore the base member can directly support the indicator member(s), which is/are disposed between the cap member and base member. It should also be understood that one, two, or even more indicator members can be used to provide dosage indicia to the user.

As shown in FIG. 1, the viewing window 34 is large enough such that the dosage indicator member 260, and a second dosage indicator member if used, with their indicia are visible therein. In the operation of a second embodiment, a second indicator member rotates with each actuation of the cap member 20 relative to the base member 40 as the ratchet wheel 82 is driven by the pawl member 48. The indicator member rotates about an axis substantially perpendicular to the axial movement of the cap member relative to the base member and to the rotational axis of the indicator member. In the preferred embodiment, with the indicator member having "ones" indicia and the ratchet wheel 82 having ten teeth, the indicator member is advanced upon each actuation and provides indicia visible to the user to notify them of such advancement. As the indicator member completes a cycle, or rotation, the indicator member 260 is advanced one increment by the drive member 86 and the indicator member begins another cycle. In this way, the user is advised as to each actuation of the indicating device and the attendant dispensment of a dosage from the attached container.

Figure 4:
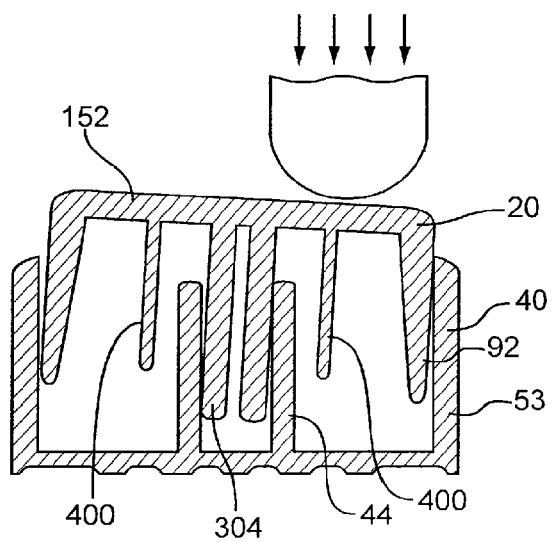
FIG. 4 is a cross-sectional view of an indicating device configured without a domed surface having an offset longitudinal force being applied thereto.

As shown in the embodiment of FIG. 4, the upper surface 152 of the first housing component is relative flat, or even concave. The user actuates the indicating device by applying a force (e.g., depressing) to the cap member at a location spaced from the center longitudinal axis 103, which is aligned with the return spring 100, 400. The off-center load, however, can lead to a tilting of the cap member relative to the base member due to the moment of the applied and resistant longitudinal forces. This tilting can lead to the center guide post 304 bending, which further leads to a frictional force between the guide post 304 and corresponding socket formed in the post 44, as well as create a friction force on opposite sides between the respective skirts or walls 92, 53 of the cap member 20 and base member 40. In addition, the coefficient of friction in plastics can increase with increased normal forces, thereby increasing the frictional forces resisting movement between the first and second housing components. This friction force, in turn, increases the force required to actuate the indicating device 10, which may then not be tuned with the actuation force of the corresponding container 12. As such, the container 12 may actuate without a corresponding actuation of the indicating device 10, thereby leading to an inaccurate counting of dispensed or remaining dosages.

Referring to FIGS. 1A-F and 3A-F, the cap member 20 is made, in one embodiment, of Acetal copolymer. In one embodiment, the cap member is made of an Acetal copolymer containing a silicone lubricant additive (e.g., 2% silicone lubricant) integrally formed therewith. It should be understood that the lubricant can also be added to the surface of the cap member, either as a separate layer applied thereto, or by applying a coating thereof. It should also be understood that lubricants other than silicone can be used, including for example and without limitation a Teflon® coating. It should be understood that the base member 40 also can be made of a material containing a lubricant, such as a lubricated polycarbonate, including without limitation PTFE and/or silicone, or the same material as the cap member, and that the lubricant(s) can be blended with a resin before molding, or applied afterwards during assembly.

In addition to the cap member and base member, other components of the indicating device, including without limitation the indicator member and drive assembly (including the ratchet wheel and drive member), can also be made of or include a lubricant, including for example a lubricated Polycarbonate (15% Teflon, 2% Silicone). The lubricant may improve the audible quality of the device, for example after the device has reached its intended end-of-life cycle. For example, in one embodiment of an end-of-use feature, the pawl is bent by the ratchet gear. In the bent condition, the pawl may rub on the ratchet teeth. In certain embodiments, the ratchet wheel and pawl are made of the same material, e.g., polycarbonate, which may tend to create friction and audible noises when rubbed together. Accordingly, lubrication of the ratchet wheel tends to improve the performance of the device in the end-of-use state. Lubrication of the indicator member may also be of benefit by reducing frictional forces during rotation. However, manufacture of the indicator member and the cap member from different materials may also reduce the amount of friction between those components. In general, friction between plastic components may be difficult to predict and often is non-linear in its response to input forces. As such, the selective use of lubricants and/or lubricated resins may provide an advantage in situations where sliding friction causes excessive force increases and/or where high predicted reliability/repeatability is important. The addition of lubricants may also improve wear, which may be of a lesser concern in devices having a limited life cycle.

Figure 14:
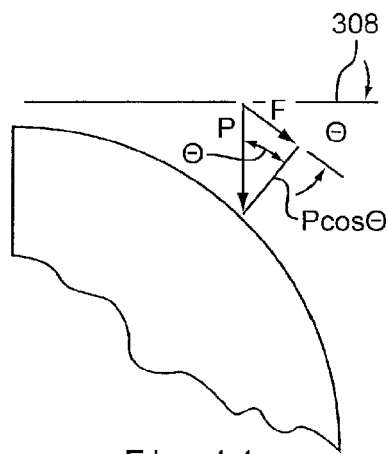
FIG. 14 is a schematic showing a force vector applied to a domed surface.

The cap member 20 has an exposed actuation surface 52 extending between the center axis 103 and an outer peripheral edge 306 of the cap member 20, defined in one embodiment as the outer surface of the skirt 92. A corner radius may be provided at the outer peripheral edge of the surface 52. The actuation surface 52 has a substantially convex domed shape such that a tangent along any point of at least the outer one half peripheral/annular portion (½ R (see FIG. 1D)) of the actuation surface 52 forms an angle ($\theta$) relative to a plane 308 formed substantially perpendicular to the axial path 103, wherein the angle is greater than 0 degrees and less than or equal to 90 degrees, or between 0 and 90 degrees (see FIG. 14). In other embodiments, the tangent along at least the outer ⅔ annular portion (⅔ R), along at least ¾ of the annular portion (¾ R), or substantially along the entire surface (R (except at the apex where $\theta$=0)) form an angle ($\theta$) with the plane 308 between 0 and 90 degrees.

The domed cap member 20 has a first height (H1) along the center axis 103 and a second height (H2) along the outer peripheral edge 306. As shown in FIGS. 1A-F, the second height (H2) also includes the height of a curved radius or shoulder portion, which has a radius of between 0.25 mm to about 3.00 mm. As shown in FIGS. 1A-F and 3A-F, the difference between the first and second heights (H1-H2) is greater than or equal to 0.50 mm and less than or equal to about 3.00 mm. Put another way, the height of the domed portion of the cap member has a height of greater than or equal to 0.50 mm and less than or equal to 3.00 mm. In one suitable embodiment, the cap member 20 has a 1.5 mm domed profile with a 2% silicone additive. In various embodiments, the actuation surface has a hemispherical profile, an elliptical profile or any other substantially similar profile.

The shape of the actuation surface 52 and coefficient of friction of the cap member 20, altered for example by the composition of the materials including the addition of lubricant, are determined such that the user has a difficult time applying a load more than 6 mm from the center 103 of the cap member. In particular, and referring to FIG. 14, the coefficient of friction is determined by the following equations:

$F = P\sin(\theta) \leq \mu\cos(\theta)$ $\eta \geq \sin(\theta)/\cos(\theta)$ $\mu \geq \tan(\theta)$ Accordingly, assuming for example a coefficient of friction of 0.2 and a 20 mm diameter cap member, a contact angle of 11.3 degrees and a dome height of 1.6 mm is calculated. As the coefficient of friction is reduced, for example by using a lubricant, the user must actuate the device closer to the center axis 103 assuming the same dome height. If the user attempts to operate the device with their fingers off center a greater distance from the axis 103, they will be required to apply a corresponding lateral force in order to retain contact with the device. Such a lateral force will produce a moment that counters the offset moment produced by the longitudinal force and the resistant biasing forces, thereby reducing the binding frictional forces. It should be understood that the domed shape and/or lubricant can be used with any type of indicating device having two housing components moving relative to each other and which are actuated by an axial force resisted by a centralized biasing force (e.g., spring 100, 400), or where the application and resistant biasing forces are offset. The dome shape is positioned preferably such that an apex thereof is proximate the axis of the biasing force (e.g., axis 103 which is aligned with springs 100, 400). It should be understood that a lubricant, whether applied to the cap member, base member or both, further reduces the frictional forces between the sliding components of the cap member and base member, including the internal guidance members (hub portion 44 and post 304) thereof, during an off-center actuation. Benefits from the lubrication may be realized even without a dome shaped cap member.

Various indicating devices and components thereof are disclosed in U.S. Pat. Nos. 6,082,358, 6,336,453 and 6,328,037, all of which are hereby incorporated herein by reference. Although the indicating device has been described herein in connection with an aerosol container, it should be understood that it can be used with other dispensing devices which are actuated, with each actuation causing a movement of the drive member.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended aims, including all equivalents thereof, which are intended to define the scope of the invention.

What is claimed is:

1. An indicating device comprising:
a first housing component adapted to be mounted to a container;
a second housing component moveably connected to said first housing component, wherein said second housing component is moveable relative to said first housing component along an axial path, wherein said second housing component comprises an exposed actuation surface extending between a center axis and an outer peripheral edge of said second housing component, said exposed actuation surface comprises a lubricant; and
an indicator member disposed in at least one of said first and second housing components.

2. The indicating device of claim 1,
wherein said exposed actuation surface has a substantially convex domed shape such that a tangent along any point of at least the outer one half peripheral portion of said exposed actuation surface forms an angle relative to a plane formed substantially perpendicular to said axial path, wherein said angle is greater than 0 degrees and less than or equal to 90 degrees, wherein at least one of said first and second housing components comprises a longitudinally extending wall, and wherein said first and second housing components comprise mating guide components disposed proximate said center axis, said guide components slidable relative to each other as said second housing component is moveable relative to said first housing component along said axial path, and wherein said mating guide components are spaced radially inwardly from said longitudinally extending wall forming a cavity between said longitudinally extending wall and said mating guide components.

3. The indicating device of claim 2 wherein said second housing component has a first height along said center axis and a second height along said outer peripheral edge, wherein the difference between said first and second heights is greater than or equal to 0.50 mm and less than or equal to about 3.00 mm.

4. The indicating device of claim 2 wherein said exposed actuation surface has a hemispherical profile.

5. The indicating device of claim 2 wherein said exposed actuation surface has an elliptical profile.

6. The indicating device of claim 2 wherein said first housing component comprises a first longitudinally extending wall and said second housing component comprises a second longitudinally extending wall, wherein said first and second walls are moveable relative to each other.

7. The indicating device of claim 1 further comprising a spring disposed interiorly of said mating guide components.

8. The indicating device of claim 1 wherein said lubricant comprises a silicone lubricant.

9. The indicating device of claim 8 wherein said at least said second housing component comprises an acetal copolymer containing said silicone lubricant.

10. An indicating device comprising:
a first housing component adapted to be mounted to a container;
a second housing component moveably connected to said first housing component, wherein said second housing component is moveable relative to said first housing component along an axial path, wherein said second housing component comprises an exposed actuation surface having a substantially convex domed shape; and
an indicator member disposed in at least one of said first and second housing components;
wherein said exposed actuation surface of said second housing component comprises a lubricant.

11. The indicating device of claim 10 wherein said lubricant comprises a silicone lubricant.

12. The indicating device of claim 11 wherein said second housing component comprises an acetal copolymer containing said silicone lubricant.

13. A method of actuating an indicating device comprising:
providing a first housing component adapted to be mounted to a container, a second housing component moveably connected to said first housing component and a biasing member disposed between said first and second housing components, wherein said second housing component comprises an exposed actuation surface extending between a center axis and an outer peripheral edge of said second housing component, wherein said exposed actuation surface of said second housing component comprises a lubricant, wherein at least one of said first and second housing components comprises a longitudinally extending wall, and wherein said first housing component comprises a first guide component and said second housing component comprises a second guide component slidably disposed relative to said first guide component, wherein said first and second guide components are disposed proximate said center axis and wherein said first and second guide components are spaced radially inwardly from said longitudinally extending wall forming a cavity between said longitudinally extending wall and said first and second guide components;

applying an axial force to an outer peripheral portion of said exposed actuation surface of said second housing component relative to said first housing component along an axial path, wherein said axial force is greater than a biasing force applied by said biasing member;

applying a lateral force to said outer peripheral portion sufficient to maintain contact with said actuation surface; and rotating an indicator member disposed in at least one of said first and second housing components in response to one or more applications said axial force.

14. The method of claim 13 wherein said exposed actuation surface has a substantially convex domed shape, and wherein a tangent along any point of at least the outer one half peripheral portion of said exposed actuation surface forms an angle relative to a plane formed substantially perpendicular to said axial path, wherein said angle is greater than 0 degrees and less than or equal to 90 degrees.

15. The method of claim 13 wherein said exposed actuation surface has a substantially convex domed shape, and wherein said second housing component has a first height along said center axis and a second height along said outer peripheral edge, wherein the difference between said first and second heights is greater than or equal to 0.50 mm and less than or equal to about 3.00 mm.

16. The method of claim 13 wherein said exposed actuation surface has a substantially convex domed shape, and wherein said actuation surface has a hemispherical profile.

17. The method of claim 13 wherein said exposed actuation surface has a substantially convex domed shape, and wherein said exposed actuation surface has an elliptical profile.

18. The method of claim 13 wherein said first housing component comprises a first longitudinally extending wall and said second housing component comprises a second longitudinally extending wall, wherein said first and second walls are moveable relative to each other, and wherein said first and second guide components are spaced radially inwardly from said first and second longitudinally extending walls.

19. The method of claim 13 wherein said lubricant comprises a silicone lubricant.

20. The method of claim 19 wherein said at least said second housing component comprises an acetal copolymer containing said silicone lubricant.

21. The method of claim 13 wherein said biasing member is disposed interiorly of said first and second guide components.

* * * * *